US005795588A

United States Patent [19]

Sauter

[11] Patent Number: 5,795,588

[45] Date of Patent: Aug. 18, 1998

[54] ENCAPSULATED PRODUCT

[75] Inventor: Erich W. Sauter, Washington Crossing, Pa.

[73] Assignee: Warner-Lambert Company, Morris Plains, N.J.

[21] Appl. No.: 323,160

[22] Filed: Oct. 14, 1994

Related U.S. Application Data

[62] Division of Ser. No. 180,550, Jan. 12, 1994, Pat. No. 5,511,361, which is a division of Ser. No. 927,066, Aug. 7, 1992, Pat. No. 5,317,849.

[51] Int. Cl.[6] .................. A61K 9/48; A61J 3/07

[52] U.S. Cl. .................. 424/451; 424/453; 424/454; 424/463; 514/962

[58] Field of Search .................. 424/454, 453, 424/463, 451; 514/962

[56] References Cited

U.S. PATENT DOCUMENTS

| | | | |
|---|---|---|---|
| 326,578 | 9/1885 | Merz | 53/900 X |
| 540,538 | 6/1895 | Colton . | |
| 961,936 | 6/1910 | Colton et al. . | |
| 1,787,777 | 1/1931 | Colton . | |
| 2,299,039 | 10/1942 | Scherer | 264/DIG. 37 X |
| 2,373,721 | 4/1945 | Taylor et al. | 91/4 |
| 2,671,245 | 3/1954 | Kath | 18/25 |
| 2,727,473 | 12/1955 | Wolff et al. | 107/1 |
| 2,936,493 | 5/1960 | Scherer | 53/281 |
| 3,078,629 | 2/1963 | Besemer et al. | 53/284.5 |
| 3,264,802 | 8/1966 | Kath | 53/900 X |
| 3,927,195 | 12/1975 | Messora | 53/900 |
| 4,667,498 | 5/1987 | Sauter | 72/100 |
| 4,820,524 | 4/1989 | Berta | 424/474 |
| 4,867,983 | 9/1989 | Berta | 424/451 |
| 4,921,108 | 5/1990 | Berta | 209/625 |
| 4,928,840 | 5/1990 | Barshay et al. | 220/8 |
| 4,936,074 | 6/1990 | Graham | 53/900 |
| 4,965,089 | 10/1990 | Sauter et al. | 427/3 |
| 4,993,137 | 2/1991 | Muto et al. | 264/DIG. 37 X |
| 5,081,822 | 1/1992 | Boyd et al. | 53/900 |
| 5,101,612 | 4/1992 | Yamamoto et al. | 53/900 X |
| 5,146,730 | 9/1992 | Sadek et al. | 53/454 |
| 5,317,849 | 6/1994 | Sauter | 53/563 X |
| 5,415,868 | 5/1995 | Smith et al. | 424/454 |
| 5,609,010 | 3/1997 | Sauter | 53/467 |

FOREIGN PATENT DOCUMENTS

| | | |
|---|---|---|
| 0279682 | 8/1988 | European Pat. Off. . |

*Primary Examiner*—Robert H. Harrison
*Attorney, Agent, or Firm*—Synnestvedt & Lechner

[57] ABSTRACT

Encapsulated small articles such as medicines in caplet or cylindrical form are disclosed. Gelatin half capsules are formed on the pins of pin blocks and are delivered to a station at which they are trimmed and fitted over the opposite ends of the product to be encapsulated. The capsule halves are first dried to a condition in which they have about 20 wt. % moisture and are thereafter press fitted over the ends of the caplets and allowed to dry to shrink fit tightly onto the caplets making it virtually impossible to remove them from their gelatin coverings without leaving visible evidence of tampering. The finished product has a smoother outer surface which lends itself to overprinting with a precise color separation line between the two capsule halves if the capsule halves are distinctly differently colored.

13 Claims, 3 Drawing Sheets

ENCAPSULATED PRODUCT

CROSS REFERENCE

This is a divisional of copending application Ser. No. 08/180,550 filed on Jan. 12, 1994, U.S. Pat. No. 5,511,361, which is a divisional of application Ser. No. 07/927,066 filed Aug. 7, 1992, now U.S. Pat. No. 5,317,849, issued Jun. 7, 1994.

FIELD OF INVENTION

This invention relates to encapsulated small articles, particularly medicines in cylindrical form, such as lozenges or caplets within a coating or covering of a gelatin or a gelatin-like substance.

BACKGROUND OF INVENTION

The dispensing of medicines and the like within readily digestible gelatin capsules is a technique which has been in use since the middle of the last century. Typically, empty gel capsules have been manufactured in two piece cylindrical form, one piece being called the body and the other the top. The capsule bodies are filled with medicine and the tops, which have a slightly larger internal diameter than the outer diameter of the body, are placed over the filled bodies for supply to the ultimate consumer.

Over the years, a strong consumer preference has developed for taking many kinds of medicine in capsule form. The encapsulated products are generally considered to be easier to swallow, since they are tasteless and the gelatin coating does not dissolve until the capsule is within the stomach, so that bitter and otherwise unpleasant tastes associated with many medicines are avoided.

Presently utilized forms of capsule-making equipment are essentially the same in operating principles and basic construction as the equipment described in Colton U.S. Pat. No. 1,787,777, issued Jan. 6, 1931, the disclosure of which is incorporated herein by reference. According to Colton, capsule-forming pins are mounted in series on elongated bars called pin bars. Pairs of pin bars, one having pins dimensioned to form capsule tops or caps and the other having pins of slightly smaller diameter and forming capsule bodies, are moved along parallel paths to a dipping bath where the pins are immersed in a liquid gelatin of conventional composition under temperature conditions which allow for the formation of a coating of gelatin on each pin. When the desired amount of coating has accumulated, the bars with the coated pins are then removed from the gelatin bath, passed through a drier and then stripped from the pins by a stripper mechanism into openings in collets or holders associated with each pin. The ends of the capsule parts are then trimmed to length after which the capsule top or cap is fitted onto the capsule body. In the form Colton machines have been used for many years, the completed empty capsules are then deposited on a conveyer belt and, after inspection, are shipped to a pharmaceutical company or pharmacy where they are taken apart, filled with medicament and, thereafter, bottled in predetermined quantities for dispensing to the ultimate user.

Another known form of encapsulation equipment is as described and claimed in U.S. Pat. No. 4,820,524, issued Apr. 11, 1989. This equipment involves modification of Colton-type machinery so that the pin blocks are replaced with caplet holders which grip the caplets and individually dip and dry first one end and then the other end of each caplet to provide a complete overcoating of gelatin.

SUMMARY OF THE INVENTION

The present invention relates to a product made with equipment used in conjunction with Colton-type capsule making machinery of the general kind described above. Essentially, the invention contemplates product involving encapsulation of solid medicaments in the form of caplets, or like substantially cylindrical shapes, in gelatin capsules wherein the gelatin capsules are formed on pin bars as substantially identically dimensioned capsule halves. The identically dimensioned halves are delivered to a station at which they are fitted over the opposite ends of the caplets, which are fed to the station in end-to-end relationship, preferably by gravity, directly from the caplet forming dies. Means and method are provided for aligning the caplets and the capsule halves in coaxial relationship and thereafter press fitting the capsule halves onto the caplets until the facing end surfaces of the capsule halves abut each other at approximately the mid point of each caplet.

In accordance with a preferred embodiment of the invention, the capsule halves are delivered to the assembly station with a moisture content of greater than 10% and most preferably with a moisture content of at least 18%. It has been found that when the caplets are encapsulated within gelatin capsules having such a relatively high moisture content, the gelatin capsule parts dry to shrink fit tightly onto the caplets making it virtually impossible to remove a caplet from within its gelatin covering without leaving plainly visible evidence of tampering.

OBJECTS AND ADVANTAGES OF THE INVENTION

Caplet encapsulation according to the teachings of the invention affords numerous advantages which are achieved by the use of identical half capsules which are fitted over a capsule with the end surfaces engaging one another. The encapsulated product has a smooth outer surface which can be easily overprinted, presents an attractive appearance and is difficult to open without exhibiting evidence of tampering. Since there is no overlap of the two halves of the semitransparent gelatin, one advantage of the invention is the capability of providing a precise color separation line when the two halves are differently colored for identification purposes.

An objective of the invention is the provision of equipment and method which avoid production of products having hidden defects. In use of the techniques of the invention, if the caplets are broken or otherwise deformed in the automatic machinery, it is virtually impossible to encapsulate them so that an encapsulated product having a hidden defect is virtually impossible to make. For similar reasons, if caplets are not delivered to the encapsulation station, the capsule halves cannot be joined so that empty capsules will not be inadvertently delivered to the end user.

Another important objective of the invention is the minimization of caplet handling prior to encapsulation. Advantages of this are the reduction of dust formed and an avoidance of chipping or breakage of caplets. Any dust which is formed as the caplets are conveyed to the encapsulation station can be readily withdrawn from the environment by a simplified form of vacuum equipment connected to the caplet delivery means.

Additional objectives are simplification of encapsulating equipment, higher production rates and a minimization of machine wear.

The above and other objects and advantages will become apparent from the following detailed description of the preferred embodiment of the invention.

DETAILED DESCRIPTION OF THE DRAWINGS

DETAILED DESCRIPTION OF THE EMBODIMENT OF THE INVENTION

Figure 1:
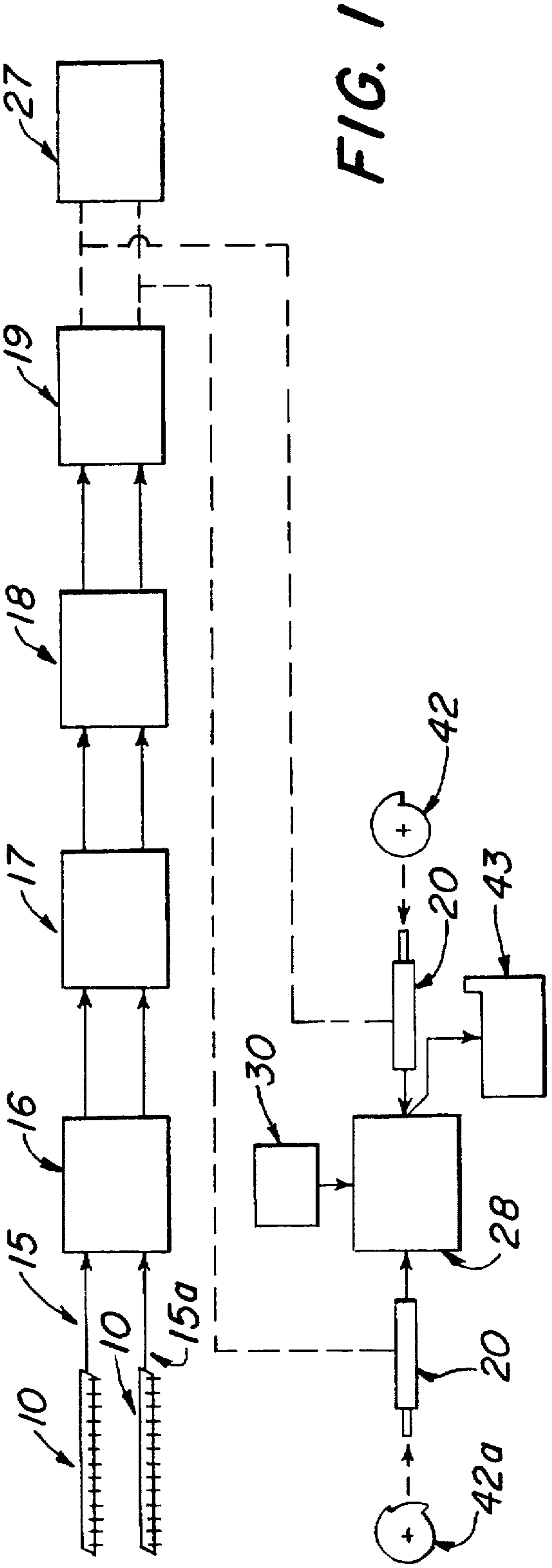
FIG. 1 is a schematic representation of equipment and method incorporating the invention.
Figure 2:
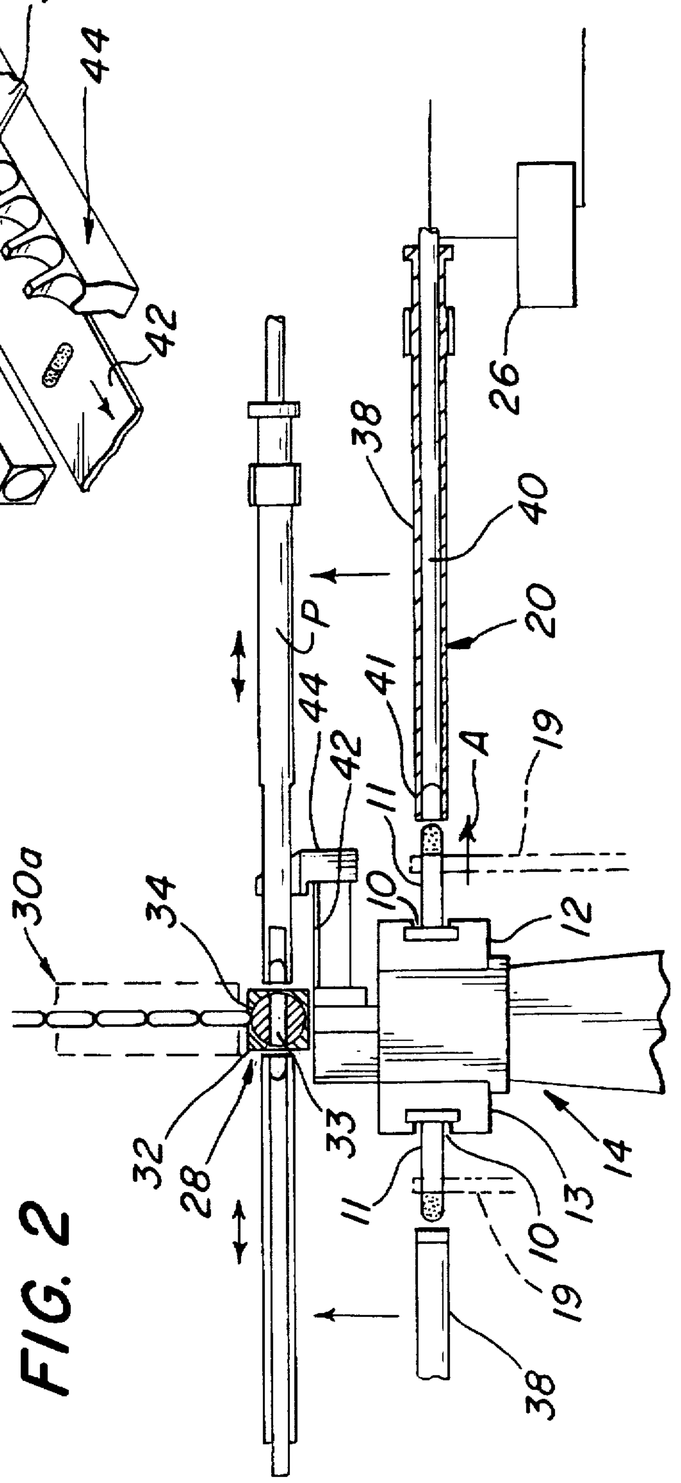
FIG. 2 is an elevational view of equipment formed in accordance with the invention.
Figure 5:
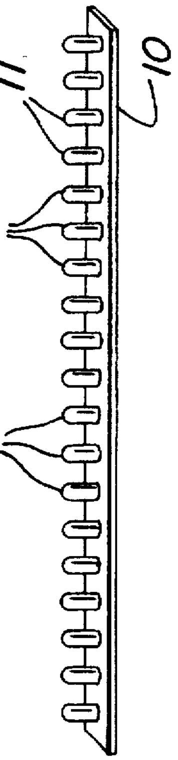
FIG. 5 is a perspective view of a pin bar of the type illustrated and utilized in the equipment of FIGS. 2 and 3.

Turning now to a detailed description of the presently preferred embodiment of the invention, FIG. 1 shows a flow chart illustrating equipment and FIG. 2 shows a side view of encapsulation equipment with a pair of pin bars 10 disposed in side-by-side relationship with pins 11 facing outwardly with respect to one another. From FIG. 5, it can be seen that each pin bar 10 consists of an elongated base plate and a multiplicity of pins 11 on which gelatin capsule halves are intended to be formed. Each pin 11 is substantially cylindrical with a curved tip, and each has an outer diameter slightly greater than the diameter of the object to be encapsulated. The pins are preferably slightly tapered toward their free ends to facilitate removal of the gelatin capsule parts from the pins, as will be described later on.

The use of the pin bars in forming capsule parts and the equipment for transporting the bars to the point where the capsule pieces are stripped into holders or collets are of substantially conventional construction and are as is described in Colton U.S. Pat. No. 1,787,777, which patent is herein incorporated by reference. In the present invention, the capsule parts are used in the encapsulation of medicines in a solid, substantially cylindrical form commonly referred to as a caplet, and the term caplet is intended to be used broadly as meaning a solid object formed of a medicament or like substance having an elongated, generally cylindrical cross-section with ends which are usually, but not necessarily, rounded.

Figure 3:
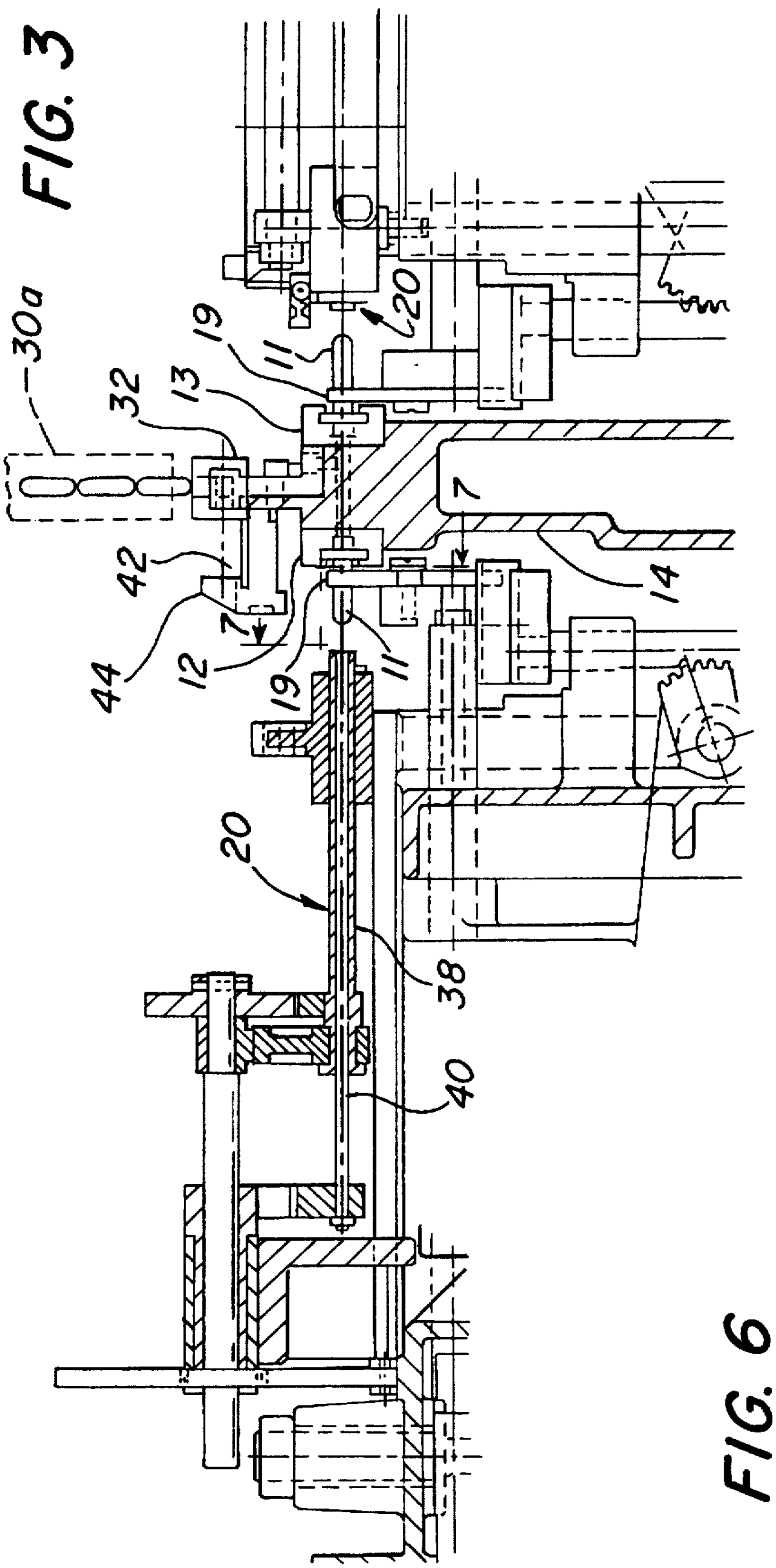
FIG. 3 is an elevational view of the opposite side of the equipment of FIG. 2.

As illustrated in FIGS. 2 and 3, pin bars 10 are shown as slideably mounted in outwardly facing guide tracks 12 and 13 mounted on a support 14 of the conventional Colton-type machine.

By way of general explanation of the conventional equipment, as modified according to the present invention, the schematic of FIG. 1 illustrates the sequence of steps of the pin bars as they pass in parallel paths 15,15*a* first to a pin lubricating station 16 where a lubricant is applied to each pin, followed by a dipping station 17 in which they are immersed in a gelatin bath until a coating of gelatin of the desired thickness is accumulated. After removal from the gelatin bath, the pin bars 10 are moved to a drying station 18 wherein warm air is circulated for curing and hardening of the gelatin. Once the capsule parts have dried the requisite amount, as explained below, they are stripped from the pins by stripping devices, generally indicated at 19, and deposited in collets 20.

Upon delivery of the capsule parts to the station shown in FIGS. 1 and 2 where they are positioned to be stripped from pins 11, they have hardened to the point where they can be removed from the pins without damage but still are relatively moist. For reasons explained hereinafter, it is preferred that the gelatin capsule parts, at the point of placement onto the caplets, have a moisture content of at least 10% and preferably greater than about 20%. The upper limit of moisture content can be determined by a few field trials. Generally, moisture content of over about 25% yields capsule parts which are apt to be too delicate for handling without some distortion and damage.

As noted above, as distinguished from prior art pin blocks having pins on which the capsule caps or tops are formed to fit over the capsule bodies, the pins in the blocks in guide tracks 12 and 13 have identical diameters so that identically sized capsule halves are formed thereon.

Figure 7:
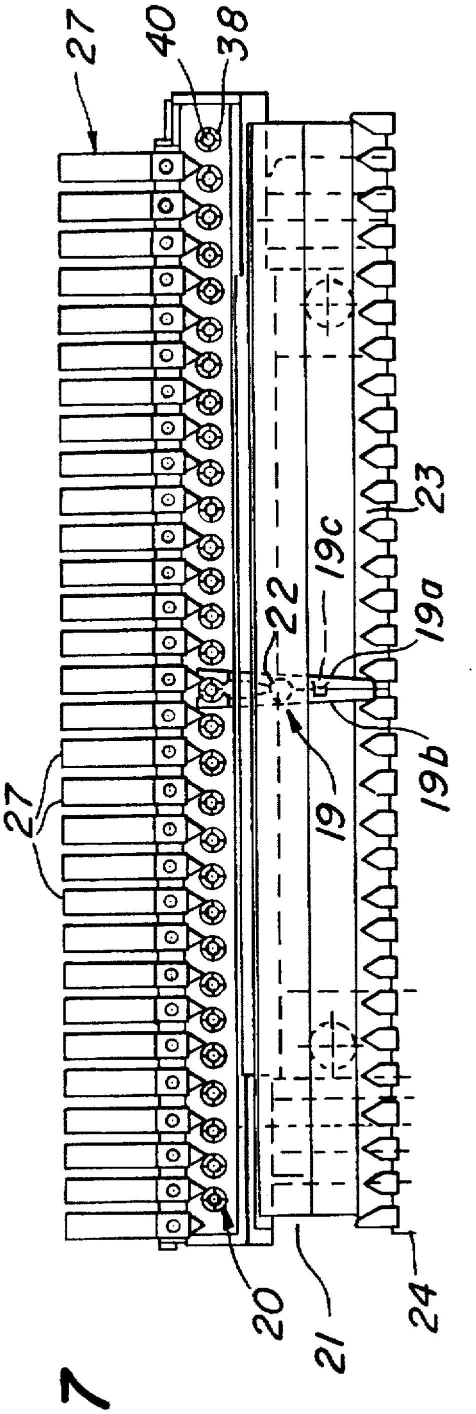
FIG. 7 is a view taken on lines 8—8 of FIG. 3.

The reciprocating strippers 19 are of conventional construction and are associated with each pin of the pair of pin bars shown in FIG. 2. As best seen in FIG. 7, each stripper 19 comprises a pair of pivotally interconnected arms 19*a* and 19*b* which are mounted on a transversely extending bar 21 by suitable pivot pins 22. The strippers 19 are each spring loaded together by a spring 19*c* so that they yieldably fit over an associated pin. The strippers, one of which is also shown in broken lines in FIG. 2, are initially held open by wedges 23 mounted on a holder bar 24 and are first moved vertically to positions in which they fit over each individual pin 11. Thereafter the lower ends are freed from the wedges and the springs 19*c* allow them to close over each pin as is known in the art. They are then moved laterally as indicated by arrow A in FIG. 2 by cam means so that each strips its capsule half off the end of the associated pin 11 into a coaxially aligned opening 25 in each tubular holders or collet 20, there again being one collet for each pin of the pair of pin blocks positioned, as shown in FIG. 2.

Once the collets 20 have received a capsule half within each opening 25, the collets are raised in unison by means such as a rack and gear segment mechanism represented diagrammatically by block 26 in FIG. 2. As the collets 20 are moved upwardly, the open end of each capsule half is trimmed to length by a knife 27, there being one knife 27 for each collet 20 as is shown in FIG. 7. As is explained in the above described Colton patent, the collets 20 are rotated against the knives to trim the capsule pieces to precise length. Each collet is raised to a position in a plane "P" so that it is in alignment with the ends of a caplet at a caplet holding station 28, as is explained with reference to FIG. 2 and as illustrated schematically in perspective in FIG. 4.

Figure 4:
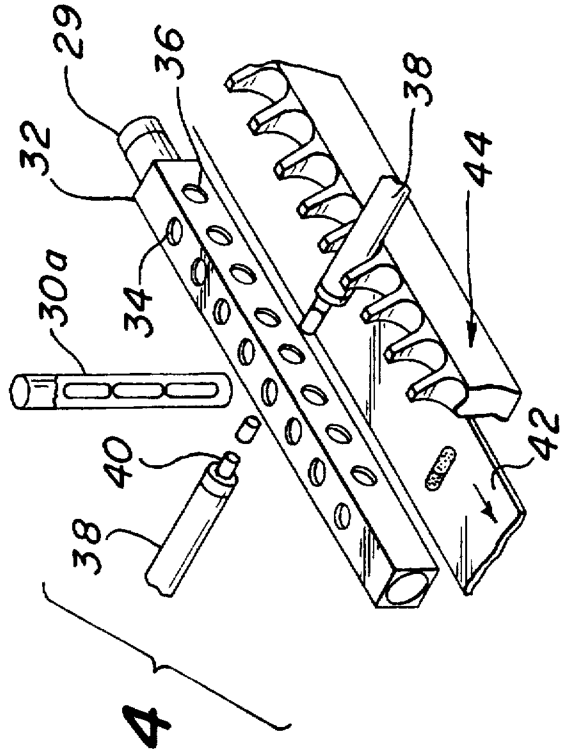
FIG. 4 is a perspective view of key components of the invention shown in FIGS. 2 and 3.

According to the invention, the caplets are formed and fed by caplet forming and feed means 30 which may include a caplet press of known construction and a plurality of tubular guide chutes 30*a*, one of which is illustrated in FIGS. 2–4. The guide chutes deliver the caplets to the caplet holding station 28 where they are properly oriented so that the step of encapsulation can be performed. As can be seen in FIG. 2, the holding station includes means which preferably comprises an elongated cylindrically shaped turning bar 29, rotatably mounted within the cylindrical bore of an elongated fixed support 32, which in turn is spatially located intermediate the two rows of collets 20.

As can be seen again with reference to FIGS. 2 and 4, turning bar 29 is provided with a multiplicity of diametrically extending throughbores 33, each of which is sized to receive a caplet from an associated guide chute 30*a* and is moveable by rotation of the turning bar from the vertical position in which it receives the caplet.

The elongated fixed support 32 is similarly provided with a first series of openings in its upper surface, as shown at 34, there being one opening 34 for each throughbore 33, with the openings 34 in registry with throughbore 33 when the turning bar is in a position in which the throughbores are vertically oriented. As indicated above, the caplet dispensing means 30 is located immediately above the turning bar 29. The caplet dispensing means 30, which may include a caplet forming press, comprises a multiplicity of side-by-side tubular caplet chutes 30*a* which are configured to deliver the caplets one at a time in end-to-end relationship through each of the openings 34 in the elongated fixed support 32. When the throughbores 33 are in the vertical position in coaxial alignment with the openings 34, the caplets pass through each opening 34 and are stopped by the lowermost surface of the support 32. In this position, the caplets are wholly within the throughbores 33, and the turning bar is ready to be rotated to a position of alignment with the collets 20.

As shown in FIGS. 2 and 4, upon rotation of the turning bar 29 through an angle of 90°, the caplets are horizontally disposed. In this position, the ends of the throughbores 33 are in registry with horizontally disposed openings 36 in the sides of the support 32, and the caplets are in coaxial alignment with the collets 20, as is seen in FIGS. 2 and 4.

Each collet 20 is of two piece construction with an outer sleeve portion 38 having an internal diameter sized to receive one half of a capsule, as generally explained above. The collet is further provided with an inner push rod portion 40 having a concave tip 41 shaped to conform to the closed end of a capsule half. Each push rod 40 is moveable relative to the sleeve portion 38 by cam means schematically illustrated in FIG. 1 at 42 and 42*a* to eject a capsule half disposed therein. With the collets in the raised position, shown in FIG. 2, advancement of the push rods move the capsule halves toward one another through the horizontally disposed openings 36 and onto the ends of caplets present in the throughbores 33.

The capsule halves have internal diameters substantially equal to the outer diameter of the caplets and, following trimming by the knives as above described, meet and align substantially at the mid point of each caplet so that their end surfaces abut one another with the caplet completely filling the space within the capsule. When the capsule halves are delivered to the caplets with a moisture content of at least 20%, the capsule halves continue to cure and shrink-fit tightly onto each caplet so that they cannot be removed without leaving some evidence of tampering, which can be readily detected by an inspector and ultimately by the end user. If a caplet is not delivered through its guide chute, the capsule halves do not join together since joinder is dependent upon the presence of a caplet and empty capsules are not unwittingly delivered to a patient.

It can be seen from FIG. 1 that the cam means 42*a* are two step cams so as to provide for ejection of the capsules from throughbores 33 following encapsulation. Thus, the cam means 42*a* advance the push nods 40 on one side of the turning block an additional distance so as to eject the encapsulated capsules and deposit them onto conveyor belt 43, as best seen in FIGS. 3 and 4. Preferably, a belt guide 44 extends lengthwise of the conveyor belt on the side opposite to the turning bar 29 to assure that the ejected capsules remain on the belt. Following ejection of the encapsulated product, the turning bar is returned to the position in which the throughbores are oriented vertically, the next pair of pin blocks is positioned beneath station 28 with the pins in axial alignment with collets 20 and the operations described above are repeated.

In summary, with reference to FIG. 1, pin bars in pairs are successively delivered to pin lubrication station 16, to a gelatin bath 17 where the gelatin coating accumulates on the pins to form capsule halves, to a capsule drying station 18, thereafter to a capsule stripper station 19 where the capsule halves are stripped from the pins of the pair of pin blocks into the collet holders 20. The collet holders are then moved into position of alignment with the throughbores of the caplet holding means. The caplets having been delivered from the caplet dispensing means 30 which has deposited caplets in each of the throughbores 33. With the caplets oriented in the horizontal position in axial alignment with the caplet halves within the collets 20, the push rods within the caplet holders press the capsule halves axially onto the caplets in each throughbore. Thereafter, the collets are returned to positions of axial alignment with the pins of the next set of pin blocks, and the encapsulated caplets are ejected from the turning bar for deposit on conveyor 42.

The equipment is simplified with respect to the prior art and extremely reliable. Since minimal handling of caplets is involved prior to encapsulation, very little dust is produced, and such dust as is produced can be conveniently evacuated by vacuum means in communication with each caplet chute. Since effective encapsulation depends to a large degree on the delivery of well formed caplets to the caplet holding means, encapsulation of defective caplets is difficult if not impossible. If no caplet is delivered due to a jamming of caplets within one of the chutes 30*a*, the caplet halves will not be joined together, and the two halves will simply be deposited on the conveyor belt where they will be readily detected. In either case, the encapsulation of broken caplets or parts of caplets or the deposit on the conveyor belt of empty caplets, both of which are difficult to detect by inspectors, are avoided.

Figure 6:
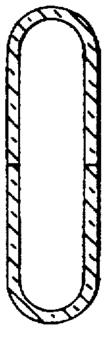
FIG. 6 is a side view of a caplet encapsulated in accordance with the teachings of the present invention.

It has further been found that when the capsule halves of a pair of capsule halves are differently colored, a sharp color line is maintained between the two capsule halves of an encapsulated product. This yields a more attractive end product and facilitates the use of different colors for color coding. Thus, encapsulated product of smooth outer surface as illustrated in FIG. 6 and having the capsule halves tightly adhered to the caplet is produced.

We claim:

1. An encapsulated product comprising:

a solid caplet;

a first gelatin capsule part having an open end and a hollow interior of cross-section substantially equal to the cross-section of said caplet;

a second gelatin capsule part having an open end and a hollow interior of cross-section equal to the first;

said hollow interior of said first and second capsule parts having a combined length substantially equal to the length of said caplet; and said capsule parts being fitted over said caplet and having said open ends in abutting relationship with each other.

2. An encapsulated product according to claim 1, wherein said capsule parts are substantially cylindrical and have substantially identical outer diameters.

3. An encapsulated product according to claim 2, wherein said capsule parts are of colors distinctly different from each other.

4. An encapsulated product according to claim 3, wherein said capsule parts are shrink fitted onto said caplet.

5. An encapsulated product according to claim 2, wherein said capsule parts have a moisture content in excess of about 18% when fitted over said caplet and a final moisture content of about 10% when stored and being characterized by about a 10% decrease in internal cross-sectional dimension at the lower moisture content, the capsule halves being substantially incapable of removal from the caplet when the encapsulated product is stored at the lower moisture content.

6. An encapsulated product according to claim 5, wherein said capsule parts are of substantially identical lengths.

7. An encapsulated product according to claim 6, wherein said product is a medicinal product.

8. A medicament comprising:

(a) a solid, generally cylindrical caplet with a longitudinal axis and having a first and a second end at opposite ends of said longitudinal axis;

(b) a first hard-shell gelatin capsule half shrink-wrapped on said second end of said caplet;

(c) a second hard-shell gelatin capsule half shrink-wrapped on said first end of said caplet and abutting, but not overlapping, said shrink-wrapped first hard-shell gelatin capsule half wherein said first and second hard-shell gelatin capsule halves have substantially the same diameter.

9. The medicament of claim 8, wherein said first and second shrink-wrapped capsule halves abut at about a midway point of said longitudinal axis of said medicament.

10. A medicament comprising:

(a) a solid caplet having a first and a second end, said caplet comprising a generally cylindrical shape;

(b) a first hard-shell gelatin capsule half of a first color shrink-wrapped on said second end of said caplet;

(c) a second hard-shell gelatin capsule half, of a color different from said first color, shrink-wrapped on said first end of said caplet and abutting, but not overlapping, said shrink-wrapped first hard-shell gelatin capsule half at about a midway point of a longitudinal axis of said medicament wherein said first and second hard-shell gelatin capsule halves have substantially the same diameter.

11. The medicament as defined in claim 8, wherein said first hard-shell gelatin capsule half has a first color and said second hard-shell gelatin capsule half has a color different than said first color.

12. An encapsulated product comprising:

a solid, generally cylindrically shaped caplet with a longitudinal axis and having a first and a second end at opposite ends of said longitudinal axis;

first and second hard-shell gelatin capsule halves shrink-fitted on said first and second capsule ends; and said shrink-fitted first and second gelatin capsule halves having substantially the same diameter and abutting but not overlapping each other.

13. The medicament as defined in claim 12, wherein said first hard-shell capsule half has a first color and said second hard-shell gelatin capsule half has a color different than said first color.

* * * * *